United States Patent [19]

Calva-Pellicer

[11] 3,966,558

[45] June 29, 1976

[54] DEVICE FOR COLLECTION OF SAMPLES FOR MICROBIOLOGICAL STUDIES

[76] Inventor: Cesar Calva-Pellicer, Copenhague No. 24, Mexico City 6, Mexico

[22] Filed: May 5, 1975

[21] Appl. No.: 574,388

[30] Foreign Application Priority Data

Nov. 5, 1974  Mexico .............................. 154796

[52] U.S. Cl. ................................ 195/139; 195/127
[51] Int. Cl.² ....................................... C12B 1/00
[58] Field of Search ............ 195/127, 139; 128/2 W

[56] References Cited
UNITED STATES PATENTS

| | | | |
|---|---|---|---|
| 2,835,246 | 5/1958 | Boettger ............................ | 128/2 W |
| 3,783,104 | 1/1974 | Henshilwood et al. ............. | 195/139 |
| 3,800,781 | 4/1974 | Zalucki .............................. | 128/2 W |

Primary Examiner—Alvin E. Tanenholtz
Attorney, Agent, or Firm—Albert L. Jeffers; Roger M. Rickert

[57] ABSTRACT

A device for collecting samples for microbiological studies in which a holder, or stopper member, is provided having a rod extending therefrom to which a cotton swab, or the like, can be connected. The holder, or stopper member, includes a first region adapted for sealing engagement with the neck of an inner container, or tube, surrounding the swab to keep the swab in a sterile condition. An outer container, or tube, is also provided which surrounds the inner container and which is also adapted for sealing engagement with the holder, or stopper member. The outer container is adapted for receiving a nutrient medium. When the containers are removed and a microbiological sample is taken by the swab, the outer container can immediately be replaced on the holder thereby maintaining the swab in uncontaminated condition and with the sample taken by the swab in the presence of a medium which will preserve the growth potential of the sample.

5 Claims, 2 Drawing Figures

DEVICE FOR COLLECTION OF SAMPLES FOR MICROBIOLOGICAL STUDIES

The present invention relates to the collection of samples, or specimens, for microbiological studies and similar studies. More particularly, the present invention relates to an improved device for the collection of such samples, or speciments, and for the maintaining thereof isolated from contaminating conditions while preserving the growth potential of the sample.

It is common practice, especially in the medical arts, to take samples of microbiological material for study, for reference to clinical pathology laboratories, and in clinics, and the like. The sample is generally taken through the use of a manually prepared swab, such as a cotton swab, and after the sample is taken, the swab is preserved in a test tube which has the open end plugged with a wad of cotton, or the like.

The procedure described above can provide no guarantee that the sample taken will not become contaminated so that the results from subsequent study can be erroneous. Further, a sample taken in the described manner is not maintained in any nutrient medium suitable for the growth or preservation of the sample taken and for this reason the procedure is further defective.

Having the foregoing in mind, an object of the present invention is to provide an improved device for taking microbiological samples and for maintaining the sample free of contamination and in a viable condition until a study can be made thereof.

A still further object of the present invention is the provision of a device of the nature referred to which is extremely convenient to use and to store.

A still further object of the present invention is the provision of a device of the nature referred to which includes adjustable features which can be beneficial in respect of the taking and the preservation of a sample.

It is also an object of the present invention to provide a device of the nature referred to which can be maintained in a sterile or aseptic condition without any problems.

BRIEF SUMMARY OF THE INVENTION

According to the present invention, a device is provided for taking microbiological samples, and the like, in which a swab element is mounted on the end of a rod. The rod is movably mounted for adjustment in a stopper-like holder member, with the holder member at the end thereof nearest the swab being provided with shouldered portions. The smaller shoulder portion nearest the swab is adapted sealingly to engage the neck of a tube in which the swab is disposed. The next largest shouldered portion of the holder, or stopper, is adapted for sealing engagement with the neck of a larger tube surrounding the first mentioned tube and somewhat longer and adapted at the closed end for receiving a nutrient medium.

In use, the tubes are removed from the holder and a sample is taken and the larger tube is then replaced on the holder member, thus disposing the sample taken in an aseptic environment and adjacent a nutrient medium therefor. The rod is axially movable in the holder and this permits the sample taken to be placed in direct engagement with the nutrient medium if advisable.

The exact nature of the present invention will become more apparent upon reference to the following detailed description taken in connection with the accompanying drawings, in which.

DETAILED DESCRIPTION OF THE INVENTION

Figure 1:
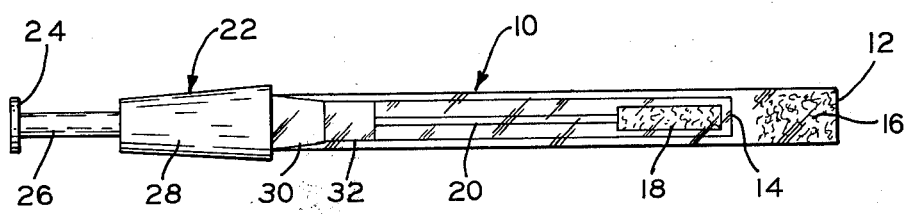
FIG. 1 is a somewhat schematic side view of the device of the present invention.

Referring to the drawings somewhat more in detail, the device according to the present invention in fully assembled position is indicated at 10. The device is arranged especially for the collection and conservation of microbiological samples, and the like, for subsequent study and analysis and is operable for maintaining the taken sample in viable condition for the period of time necessary to undertake the study.

Device 10, as will be seen in FIG. 1, includes an outer container or tube 12 which, in FIG. 1, will be seen to be closed at the right hand while at the left end the tube 12 is adapted for engagement with a holder, or stopper member, to be described hereinafter. Inside tube 12 is a second container, or tube, 14 smaller in diameter and shorter than tube 12 and also closed at the right end, while at the left end tube 14 is adapted for engagement by the aforementioned holder, or stopper member.

The space 16 between the closed ends of tubes 12 and 14 is adapted for receiving a preserving or nuitrient medium for the conservation of a sample taken, as will be described hereinafter.

The nutrient medium, for example, may be in liquid form and impregnated in a suitable sterile fibrous material disposed in the region 16 of outer tube 12.

Inside tube 14 is a swab element 18 which may be composed of any suitable neutral material, such as cotton fiber, or the like. This material is specially treated to prevent damage to any sample taken so that any samples taken can be reliably retained by the swab element 18 and without contamination.

Swab element 18 is mounted on the end of a rod, or stem, 20 which extends through a stopper member 22. Stopper member 22, which can also be considered a holder, has a smaller diameter end portion 32 adapted for sealing engagement with the open end of tube 14, while adjacent thereto is a somewhat larger diameter portion 30 adapted for sealing engagement with the open end of tube 12. At least portion 30 can be somewhat tapered inwardly toward portion 32 and each of the aforementioned portions terminates in a shoulder region which can serve as a stop for the respective tube. Holder, or stopper member, 22 is advantageously formed of a rubber-like material and can, therefore, seal inside the ends of the tubes mounted thereon.

Figure 2:
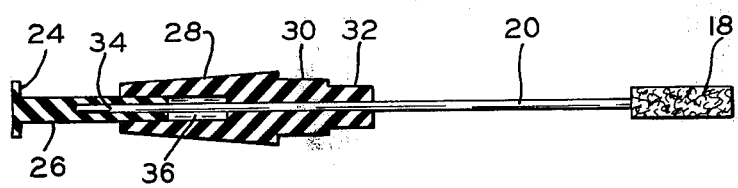
FIG. 2 is a longitudinal sectional view through the holder, or stopper member, and swab carrying element of the present invention.

Leftwardly of intermediate diameter portion 30, in the device as viewed in FIGS. 1 and 2, is an elongated portion 28 which can serve as a handle portion for stopper member 22.

Within the range of portion 28, an axial recess 36 is provided and extending into recess 36 is the cylindrical portion 26 of a knob-like element terminating in an end button 24 and fixed to the end part 34 of rod 20. Element 26 fits closely and sealingly in recess 36 but can be adjusted therein by the application of pressure to button 24 or by pulling outwardly on button 24.

From the foregoing, it will be seen that the device of the present invention is initially provided with two containers, or tubes, one inner and one outer. In assembling the device, the swab is positioned as shown in FIG. 1 and, under sterile conditions, the swab becomes enclosed in the inner container or tube 14 and is sealed within the inner tube because the tube seals on the portion 32 of the holder, or stopper member. The outer container 12 is then prepared, also under sterile conditions, and is mounted in surrounding relation to tube 14 and seals on portion 30 of the holder, or stopper member. The outer tube may at this time have a nutrient medium in space 16 thereof, or the nutrient medium may be supplied to space 16 at the time the sample is taken.

In taking a sample, the outer containers are removed from the holder, or stopper member, and if the outer tube is not already provided with appropriate nutrient in space 16, a medium will be supplied therewith.

The inner container is then removed from the holder, or stopper member, 22 thereby exposing the swab. The swab can then be employed for taking the desired sample.

After the sample is taken, the outer tube is immediately replace on the holder, or stopper member, and this will maintain the sample taken in aseptic condition and in the presence of a nutrient medium. At this time, if necessary, the button 24 is availed of to move the swab outwardly from holder, or stopper member, 22 so that the swab element will be positioned within the range of space 16 of the outer container, or tube.

It will be evident that the swab element 18 remains dry and sterile and ready for use within a tube separate and isolated from the tube for containing the preserving or nutrient medium. It is thus possible to take sample in full confidence that the sample will not become contaminated and that the sample will be preserved and can, subsequently, be reliably studied.

Modifications may be made within the scope of the appended claims.

What is claimed is:

1. In a device for collecting and preserving samples for microbiological studies and the like; a rod adapted for supporting a swab element at one end, a stopper member surrounding the rod in a region spaced from said one end and sealingly engaging the rod, an inner tubular container closed at one end and open at the other adapted for being placed over the rod from said one end of the rod and with the open end of the inner container sealingly engaging the stopper member, an outer tubular container surrounding said inner container and having an open end sealingly engaging said stopper member and a closed end axially spaced from the closed end of the inner container, said stopper member maintaining the interiors of said containers isolated from one another and from the atmosphere.

2. A device according to claim 1 in which said outer container is adapted to receive a nutrient or preservative medium near the closed end thereof and said rod being axially adjustable in said stopper member for movement of the swab into the axial range of said medium when said containers are removed and a sample taken by the swab and the outer container is replaced on the stopper member.

3. A device according to claim 1 in which said stopper member includes a first axial portion for sealing engagement with the open end of said inner container and a second axial portion for sealing engagement with the open end of said outer container.

4. A device according to claim 1 which includes means in the outer container in the axial space between the closed ends of said containers for receiving a medium compatible with the sample to be taken in respect of preservation of the growth potential of the sample.

5. A device according to claim 1 in which said rod extends axially completely through said stopper member and at the end opposite the swab end includes means for axial adjustment of the rod in the stopper member.

* * * * *